United States Patent
Herron et al.

(10) Patent No.: US 11,527,721 B2
(45) Date of Patent: Dec. 13, 2022

(54) ELECTROACTIVE MATERIALS

(71) Applicant: LG Chem, Ltd., Seoul (KR)

(72) Inventors: Norman Herron, Newark, DE (US); Weiying Gao, Landenberg, PA (US); Nora Sabina Radu, Landenberg, PA (US); Ying Wang, Wilmington, DE (US)

(73) Assignee: LG Chem, Ltd.

( * ) Notice: Subject to any disclaimer, the term of this patent is extended or adjusted under 35 U.S.C. 154(b) by 80 days.

(21) Appl. No.: 16/277,331

(22) Filed: Feb. 15, 2019

(65) Prior Publication Data
US 2019/0181344 A1 Jun. 13, 2019

Related U.S. Application Data

(63) Continuation of application No. 15/209,441, filed on Jul. 13, 2016, now abandoned.
(Continued)

(51) Int. Cl.
*H01L 51/00* (2006.01)
*C07C 211/54* (2006.01)
(Continued)

(52) U.S. Cl.
CPC .......... *H01L 51/006* (2013.01); *C07C 211/54* (2013.01); *C07C 211/61* (2013.01);
(Continued)

(58) Field of Classification Search
CPC . C07C 211/54; C07C 211/61; C07C 2603/26; C07F 7/0818; H01L 51/0052
See application file for complete search history.

(56) References Cited

U.S. PATENT DOCUMENTS

| 6,670,645 B2 | 12/2003 | Grushin et al. |
| 8,592,052 B2 | 11/2013 | Tsuji et al. |
(Continued)

FOREIGN PATENT DOCUMENTS

| JP | 2004231547 A | 8/2004 |
| JP | 2005285749 A | * 10/2005 |
(Continued)

OTHER PUBLICATIONS

Gustafsson, G., et al., "Flexible light-emitting diodes made from soluble conducting polymers." Nature, vol. 357, Jun. 11, 1992, pp. 477-479.

*Primary Examiner* — Sean M DeGuire
(74) *Attorney, Agent, or Firm* — Lerner, David, Littenberg, Krumholz & Mentlik, LLP

(57) ABSTRACT

There is disclosed a compound having Formula I

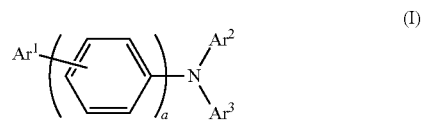

In Formula, I: $Ar^1$ is selected from the group consisting of dibenzofuran, dibenzothiophene, or deuterated analogs thereof; $Ar^2$ and $Ar^3$ are the same or different and are hydrocarbon aryl, substituted derivatives thereof, or deuterated analogs thereof, with the proviso that $Ar^2$ and $Ar^3$ are not the same as $Ar^1$; a is 0; and $Ar^1$, $Ar^2$, and $Ar^3$ have no additional amino substituents.

11 Claims, 4 Drawing Sheets

Related U.S. Application Data

(60) Provisional application No. 62/194,577, filed on Jul. 20, 2015.

(51) Int. Cl.
  | | |
  |---|---|
  | *C07C 211/61* | (2006.01) |
  | *C09K 11/02* | (2006.01) |
  | *C07F 7/30* | (2006.01) |
  | *C07F 7/08* | (2006.01) |
  | *H01L 51/50* | (2006.01) |

(52) U.S. Cl.
  CPC .............. *C07F 7/081* (2013.01); *C07F 7/30* (2013.01); *C09K 11/025* (2013.01); *H01L 51/0052* (2013.01); *H01L 51/0054* (2013.01); *H01L 51/0059* (2013.01); *H01L 51/0073* (2013.01); *H01L 51/0074* (2013.01); *H01L 51/0094* (2013.01); *H01L 51/5064* (2013.01); *H01L 2251/5384* (2013.01)

(56) References Cited

U.S. PATENT DOCUMENTS

| | | | |
|---|---|---|---|
| 2004/0102577 A1 | 5/2004 | Hsu et al. | |
| 2004/0127637 A1 | 7/2004 | Hsu et al. | |
| 2005/0184287 A1 | 8/2005 | Herron et al. | |
| 2005/0205860 A1 | 9/2005 | Hsu et al. | |
| 2006/0280965 A1* | 12/2006 | Kwong | C07C 13/62 585/27 |
| 2010/0001636 A1* | 1/2010 | Yabunouchi | C07D 307/91 313/504 |
| 2012/0068170 A1* | 3/2012 | Pflumm | C07D 413/04 257/40 |
| 2012/0119197 A1* | 5/2012 | Nishimura | C07D 209/86 257/40 |
| 2013/0150576 A1* | 6/2013 | Hotta | C07D 487/04 544/209 |
| 2013/0334517 A1 | 12/2013 | Hong et al. | |
| 2014/0151666 A1 | 6/2014 | Miyata | |
| 2015/0179951 A1 | 6/2015 | Fuchiwaki | |
| 2015/0280133 A1* | 10/2015 | Parham | C07D 413/14 257/40 |
| 2015/0280136 A1* | 10/2015 | Ryu | C09K 11/06 257/40 |

FOREIGN PATENT DOCUMENTS

| | | |
|---|---|---|
| JP | 4152761 B2 | 9/2008 |
| JP | 4377783 B2 | 12/2009 |
| JP | 2010222268 A | 10/2010 |
| KR | 20130084825 A | 7/2013 |
| WO | 2003008424 A1 | 1/2003 |
| WO | 2003040257 A1 | 5/2003 |
| WO | 2003063555 A1 | 7/2003 |
| WO | 2003091688 A2 | 11/2003 |
| WO | 2004016710 A1 | 2/2004 |
| WO | 2005052027 A1 | 6/2005 |
| WO | 2007145979 A3 | 4/2008 |
| WO | WO-2014067614 A1 * | 5/2014 ............ C07D 413/14 |

\* cited by examiner

ELECTROACTIVE MATERIALS

CLAIM OF BENEFIT OF PRIOR APPLICATION

This application claims priority under 35 U.S.C. § 120 from U.S. patent application Ser. No. 15/209,441, filed Jul. 13, 2016, which claims benefit under 35 U.S.C. § 119(e) from U.S. Provisional Application No. 62/194,577, filed on Jul. 20, 2015, both of which are incorporated by reference herein in their entirety.

BACKGROUND INFORMATION

Field of the Disclosure

The present disclosure relates to novel electroactive compounds. The disclosure further relates to electronic devices having at least one layer comprising such an electroactive compound.

Description of the Related Art

In organic electronic devices, such as organic light emitting diodes ("OLED"), that make up OLED displays, one or more organic electroactive layers are sandwiched between two electrical contact layers. In an OLED at least one organic electroactive layer emits light through the light-transmitting electrical contact layer upon application of a voltage across the electrical contact layers.

It is well known to use organic electroluminescent compounds as the light-emitting component in light-emitting diodes. Simple organic molecules, conjugated polymers, and organometallic complexes have been used. The light-emitting materials may be used alone or may be present in an electroactive host material.

Devices that use electroluminescent materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for electroactive materials for use in electronic devices.

SUMMARY

There is provided a compound having Formula I

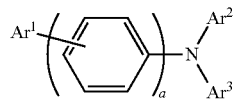

(I)

wherein:
Ar$^1$ is selected from the group consisting of phenanthrene, triphenylene, triphenylsilyl, triphenylgermyl, dibenzofuran, dibenzothiophene, polyarylphenyl, substituted derivatives thereof, and deuterated analogs thereof;
Ar$^2$ and Ar$^3$ are the same or different and are selected from the group consisting of hydrocarbon aryl, heteroaryl, substituted derivatives thereof, and deuterated analogs thereof, with the proviso that Ar$^2$ and Ar$^3$ are not the same as Ar$^1$; and
a is 0 or 1;
with the proviso that Ar$^1$, Ar$^2$, and Ar$^3$ have no additional amino substituents.

There is also provided an electronic device having at least one layer comprising a compound having Formula I.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
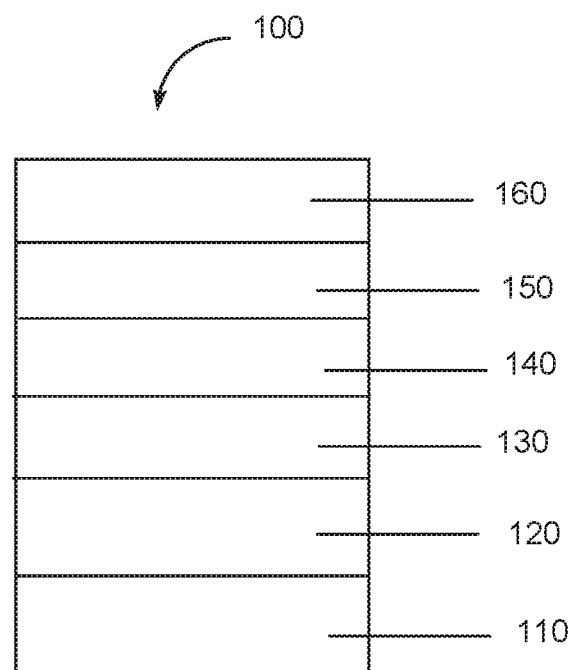
FIG. 1 includes an illustration of one example of an organic electronic device including a new compound described herein.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a compound having Formula I, as described in detail below.

There is further provided an electronic device having at least one layer comprising a compound or copolymer having any of the above formulae.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compound having Formula I, the Electronic Device, and finally Examples.

1. Definitions and Clarification of Terms

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tert-butyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aromatic compound" is intended to mean an organic compound comprising at least one unsaturated cyclic group having 4n+2 delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like.

The term "aryl" or "aryl group" means a moiety derived from an aromatic compound. The aryl group may be a single ring (monocyclic) or multiple rings (bicyclic, or more) fused together or linked covalently. Examples of aryl moieties include, but are not limited to, phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. In some embodiments, aryl groups have 6 to 60 ring carbon atoms; in some embodiments, 6 to 30 ring carbon atoms. The term is intended to include heteroaryl groups having at least one ring heteroatom. Heteroaryl groups may have from 4-50 ring carbon atoms; in some embodiments, 4-30 ring carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include D, alkyl, aryl, nitro, cyano, —N(R')(R"), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxy, siloxane, thioalkoxy, —S(O)$_2$—, —C(=O)—N(R')(R"), (R')(R")N-alkyl, (R')(R")N-alkoxyalkyl, (R')(R") N-alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups. Any of the preceding groups with available hydrogens, may also be deuterated.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "crosslinkable group" or "crosslinking group" is intended to mean a group on a compound or polymer chain than can link to another compound or polymer chain via thermal treatment, use of an initiator, or exposure to radiation, where the link is a covalent bond. In some embodiments, the radiation is UV or visible. Examples of crosslinkable groups include, but are not limited to vinyl, acrylate, perfluorovinylether, 1-benzo-3,4-cyclobutane, o-quinodimethane groups, siloxane, cyanate groups, cyclic ethers (epoxides), cycloalkenes, and acetylenic groups.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level.

The term "electroactive" as it refers to a layer or a material, is intended to indicate a layer or material which electronically facilitates the operation of the device. Examples of electroactive materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The term "germyl" refers to the group R$_3$Ge—, where R is the same or different at each occurrence and is H, D, C1-20 alkyl, deuterated alkyl, fluoroalkyl, aryl, or deuterated aryl. In some embodiments, one or more carbons in an R alkyl group are replaced with Ge.

The prefix "hetero" indicates that one or more carbon atoms has been replaced with a different atom. In some embodiments, the heteroatom is O, N, S, or combinations thereof.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "photoactive" refers to a material or layer that emits light when activated by an applied voltage (such as in a light emitting diode or chemical cell), that emits light after the absorption of photons (such as in down-converting phosphor devices), or that responds to radiant energy and generates a signal with or without an applied bias voltage (such as in a photodetector or a photovoltaic cell).

The term "siloxane" refers to the group R$_3$SiOR$_2$Si—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "siloxy" refers to the group R$_3$SiO—, where R is the same or different at each occurrence and is H, D, C1-20 alkyl, deuterated alkyl, fluoroalkyl, aryl, or deuterated aryl.

The term "silyl" refers to the group R$_3$Si—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

In a structure where a substituent bond passes through one or more rings as shown below,

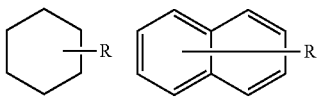

it is meant that the substituent R may be bonded at any available position on the one or more rings.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). Exemplary adjacent R groups are shown below:

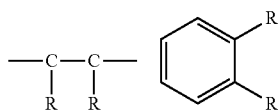

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Compound Having Formula I

In some embodiments, the electroactive compound has Formula I

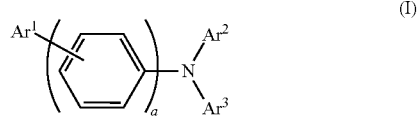

wherein:
Ar$^1$ is selected from the group consisting of phenanthrene, triphenylene, triphenylsilyl, triphenylgermyl, dibenzofuran, dibenzothiophene, polyarylphenyl, substituted derivatives thereof, and deuterated analogs thereof;
Ar$^2$ and Ar$^3$ are the same or different and are selected from the group consisting of hydrocarbon aryl, heteroaryl, substituted derivatives thereof, and deuterated analogs thereof, with the proviso that Ar$^2$ and Ar$^3$ are not the same as Ar$^1$; and
a is 0 or 1;
with the proviso that Ar$^1$, Ar$^2$, and Ar$^3$ have no additional amino substituents.

In some embodiments of Formula I, Ar$^1$, Ar$^2$, and Ar$^3$ have no carbazole or substituted carbazole substituents.

In some embodiments, the compound having Formula I is deuterated. In some embodiments, the compound is at least 10% deuterated. By "% deuterated" or "% deuteration" is meant the ratio of deuterons to the sum of protons plus deuterons, expressed as a percentage. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I, a=0.
In some embodiments of Formula I, a=1.
Ar$^1$, Ar$^2$, and Ar$^3$ have no additional amino substituents. There is a single amino group in the compound having Formula I, as shown.

In some embodiments of Formula I, Ar$^1$ is selected from the group consisting of phenanthrene, triphenylene, triphenylsilyl, triphenylgermyl, polyarylphenyl, substituted derivatives thereof, and deuterated analogs thereof.

In some embodiments of Formula I, Ar$^1$ is selected from the group consisting of triphenylsilyl, triphenylgermyl, dibenzothiophene, polyarylphenyl, substituted derivatives thereof, and deuterated analogs thereof.

In some embodiments of Formula I, $Ar^1$ is selected from the group consisting of triphenylsilyl, polyarylphenyl, substituted derivatives thereof, and deuterated analogs thereof.

In some embodiments of Formula I, $Ar^1$ is phenanthrene.

In some embodiments, the phenanthrene has Formula a

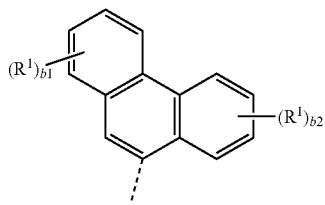

Formula a where:
R$^1$ is the same or different at each occurrence and is selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl;
b1 and b2 are the same or different and are an integer from 0-4; and
the dashed line represents a possible point of attachment.

In some embodiments of Formula a, b1=0.
In some embodiments of Formula a, b1=1.
In some embodiments of Formula a, b1=2.
In some embodiments of Formula a, b1=3.
In some embodiments of Formula a, b1=4.
In some embodiments of Formula a, b1>0 and at least one $R^1$ is D.
In some embodiments of Formula a, b1>0 and at least one $R^1$ is an alkyl or deuterated alkyl having 1-12 carbons.
In some embodiments of Formula a, b1>0 and at least one $R^1$ is an aryl or deuterated aryl having 6-18 ring carbons.
In some embodiments of Formula a, b2=0.
In some embodiments of Formula a, b2=1.
In some embodiments of Formula a, b2=2.
In some embodiments of Formula a, b2=3.
In some embodiments of Formula a, b2=4.
In some embodiments of Formula a, b2>0 and at least one $R^1$ is D.
In some embodiments of Formula a, b2>0 and at least one $R^1$ is an alkyl or deuterated alkyl having 1-12 carbons.
In some embodiments of Formula a, b2>0 and at least one $R^1$ is an aryl or deuterated aryl having 6-18 ring carbons.
In some embodiments of Formula I, $Ar^1$ is a triphenylene.
In some embodiments, the triphenylene has Formula b

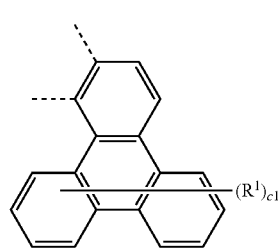

Formula b where c1 is an integer from 0-8; and $R^1$ and the dashed lines are as defined above for Formula a.

In some embodiments of Formula b, c1=0.
In some embodiments of Formula b, c1=1.
In some embodiments of Formula b, c1=2.
In some embodiments of Formula b, c1=3.
In some embodiments of Formula b, c1=4.
In some embodiments of Formula b, c1=5.
In some embodiments of Formula b, c1=6.
In some embodiments of Formula b, c1=7.
In some embodiments of Formula b, c1=8.
In some embodiments of Formula b, c1>0 and at least one $R^1$ is as described above for Formula a.

In some embodiments of Formula I, $Ar^1$ is triphenylsilyl.
In some embodiments, the triphenylsilyl has Formula c

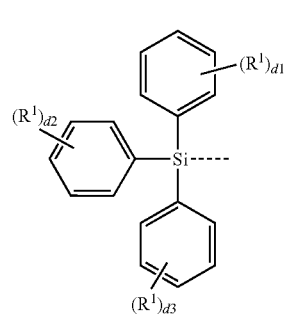

Formula c where d1, d2, and d3 are the same or different and are an integer from 0-5; and $R^1$ and the dashed line are as defined above for Formula a.

In some embodiments of Formula c, d1=0.
In some embodiments of Formula c, d1=1.
In some embodiments of Formula c, d1=2.
In some embodiments of Formula c, d1=3.
In some embodiments of Formula c, d1=4.
In some embodiments of Formula c, d1=5.
In some embodiments of Formula c, d1>0 and at least one $R^1$ is as described above for Formula a.
In some embodiments of Formula c, d2=0.
In some embodiments of Formula c, d2=1.
In some embodiments of Formula c, d2=2.
In some embodiments of Formula c, d2=3.
In some embodiments of Formula c, d2=4.
In some embodiments of Formula c, d2=5.
In some embodiments of Formula c, d2=6.
In some embodiments of Formula c, d2=7.
In some embodiments of Formula c, d2=8.
In some embodiments of Formula c, d2>0 and at least one $R^1$ is as described above for Formula a.
In some embodiments of Formula c, d3=0.
In some embodiments of Formula c, d3=1.
In some embodiments of Formula c, d3=2.
In some embodiments of Formula c, d3=3.
In some embodiments of Formula c, d3=4.
In some embodiments of Formula c, d3=5.
In some embodiments of Formula c, d3=6.
In some embodiments of Formula c, d3=7.
In some embodiments of Formula c, d3=8.
In some embodiments of Formula c, d3>0 and at least one $R^1$ is as described above for Formula a.

In some embodiments of Formula I, $Ar^1$ is triphenylgermyl.

In some embodiments, the triphenylgermyl has Formula d

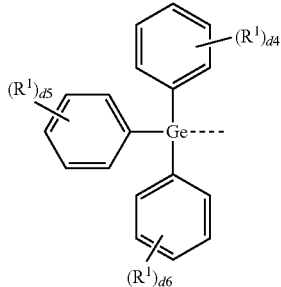

Formula d where d4, d5, and d6 are the same or different and are an integer from 0-5; and $R^1$ and the dashed line are as defined above for Formula a.

In some embodiments of Formula d, d4=0.
In some embodiments of Formula d, d4=1.
In some embodiments of Formula d, d4=2.
In some embodiments of Formula d, d4=3.
In some embodiments of Formula d, d4=4.
In some embodiments of Formula d, d4=5.
In some embodiments of Formula d, d4>0 and at least one $R^1$ is as described above for Formula a.
In some embodiments of Formula d, d5=0.
In some embodiments of Formula d, d5=1.
In some embodiments of Formula d, d5=2.
In some embodiments of Formula d, d5=3.
In some embodiments of Formula d, d5=4.
In some embodiments of Formula d, d5=5.
In some embodiments of Formula d, d5>0 and at least one $R^1$ is as described above for Formula a.
In some embodiments of Formula d, d6=0.
In some embodiments of Formula d, d6=1.
In some embodiments of Formula d, d6=2.
In some embodiments of Formula d, d6=3.
In some embodiments of Formula d, d6=4.
In some embodiments of Formula d, d6=5.
In some embodiments of Formula d, d6>0 and at least one $R^1$ is as described above for Formula a.
In some embodiments of Formula I, $Ar^1$ is a dibenzofuran.
In some embodiments, the dibenzofuran has Formula e

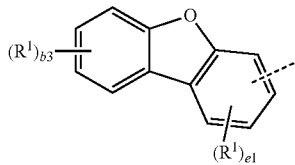

Formula e where b3 is an integer from 0-4, e1 is an integer from 0-3, and $R^1$ and the dashed line are as defined above for Formula a.

In some embodiments of Formula e, b3=0.
In some embodiments of Formula e, b3=1.
In some embodiments of Formula e, b3=2.
In some embodiments of Formula e, b3=3.
In some embodiments of Formula e, b3=4.
In some embodiments of Formula e, b3>0 and at least one $R^1$ is as described above for Formula a.

In some embodiments of Formula e, e1=0.
In some embodiments of Formula e, e1=1.
In some embodiments of Formula e, e1=2.
In some embodiments of Formula e, e1=3.
In some embodiments of Formula e, e1>0 and at least one $R^1$ is as described above for Formula a.
In some embodiments of Formula I, $Ar^1$ is a dibenzothiophene.
In some embodiments, the dibenzothiophene has Formula f

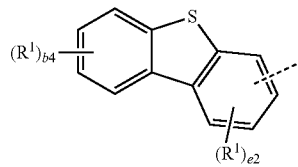

Formula f where b4 is an integer from 0-4, e2 is an integer from 0-3, and $R^1$ and the dashed line are as defined above for Formula a.

In some embodiments of Formula f, b4=0.
In some embodiments of Formula f, b4=1.
In some embodiments of Formula f, b4=2.
In some embodiments of Formula f, b4=3.
In some embodiments of Formula f, b4=4.
In some embodiments of Formula f, b4>0 and at least one $R^1$ is as described above for Formula a.
In some embodiments of Formula f, e2=0.
In some embodiments of Formula f, e2=1.
In some embodiments of Formula f, e2=2.
In some embodiments of Formula f, e2=3.
In some embodiments of Formula f, e2>0 and at least one $R^1$ is as described above for Formula a.
In some embodiments of Formula I, $Ar^1$ is a polyarylphenyl.
In some embodiments, the polyarylphenyl has Formula g

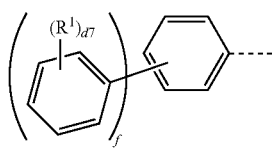

Formula g where d7 is an integer from 0-5, f is an integer of 2-4; and $R^1$ and the dashed line are as defined above for Formula a.

In some embodiments of Formula g, d7=0.
In some embodiments of Formula g, d7=1.
In some embodiments of Formula g, d7=2.
In some embodiments of Formula g, d7=3.
In some embodiments of Formula g, d7=4.
In some embodiments of Formula g, d7=5.
In some embodiments of Formula g, d7>0 and at least one $R^1$ is as described above for Formula a.
In some embodiments of Formula g, f=2.
In some embodiments of Formula g, f=3.
In some embodiments of Formula g, f=4.
In some embodiments of Formula I, $Ar^2$ and $Ar^3$ are hydrocarbon aryl groups having no fused rings, substituted derivatives thereof, or deuterated analogs thereof.

In some embodiments of Formula I, Ar² is a hydrocarbon aryl group or deuterated hydrocarbon aryl group having 6-30 ring carbon atoms; in some embodiments, 6-18 ring carbon atoms.

In some embodiments of Formula I, Ar² is a hydrocarbon aryl group having no fused rings.

In some embodiments of Formula I, Ar² is a hydrocarbon aryl group having no substituents.

In some embodiments of Formula I, Ar² is a deuterated hydrocarbon aryl group having no additional substituents.

In some embodiments of Formula I, Ar² is a hydrocarbon aryl group having one or more substituents selected from the group consisting of D, F, CN, alkyl, fluoroalkyl, heteroaryl, silyl, germyl, alkoxy, aryloxy, fluoroalkoxy, siloxane, siloxy, deuterated alkyl, deuterated partially-fluorinated alkyl, deuterated heteroaryl, deuterated silyl, deuterated germyl, deuterated alkoxy, deuterated aryloxy, deuterated fluoroalkoxy, deuterated siloxane, and deuterated siloxy.

In some embodiments of Formula I, Ar² is a hydrocarbon aryl group having one or more substituents selected from the group consisting of D, F, CN, alkyl, fluoroalkyl, silyl, germyl, deuterated alkyl, deuterated partially-fluorinated alkyl, deuterated silyl, and deuterated germyl.

In some embodiments of Formula I, Ar² has Formula h

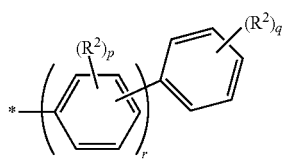

Formula h where:
R² is the same or different at each occurrence and is selected from the group consisting of D, F, CN, alkyl, fluoroalkyl, hydrocarbon aryl, heteroaryl, silyl, germyl, alkoxy, aryloxy, fluoroalkoxy, siloxane, siloxy, deuterated alkyl, deuterated partially-fluorinated alkyl, deuterated hydrocarbon aryl, deuterated heteroaryl, deuterated silyl, deuterated germyl, deuterated alkoxy, deuterated aryloxy, deuterated fluoroalkoxy, deuterated siloxane, and deuterated siloxy, where adjacent R² groups can be joined together to form an fused aromatic ring or a deuterated fused aromatic ring;

p is the same or different at each occurrence and is an integer from 0-4;

q is an integer from 0-5;

r is an integer from 1 to 5; and indicates the point of attachment.

In some embodiments of Formula h, R² is the same or different at each occurrence and is selected from the group consisting of D, F, CN, alkyl, fluoroalkylsilyl, germyl, deuterated alkyl, deuterated partially-fluorinated alkyl, deuterated silyl, and deuterated germyl, where adjacent R² groups can be joined together to form an fused aromatic ring or a deuterated fused aromatic ring In some embodiments of Formula h, p=0.
In some embodiments of Formula h, p=1.
In some embodiments of Formula h, p=2.
In some embodiments of Formula h, p=3.
In some embodiments of Formula h, p=4.
In some embodiments of Formula h, p>0 and at least one R² is D.

In some embodiments of Formula h, p>0 and at least one R² is an alkyl or deuterated alkyl having 1-12 carbon atoms.

In some embodiments of Formula h, p>0 and at least one R² is silyl or deuterated silyl.

In some embodiments of Formula h, p>0 and at least one R² is germyl or deuterated germyl.

In some embodiments of Formula h, p>0 and at least one R² is heteroaryl. In some embodiments the heteroaryl is derived from a compound selected from the group consisting carbazole, substituted derivatives thereof, and deuterated analogs thereof.

In some embodiments of Formula h, r=0.
In some embodiments of Formula h, r=1.
In some embodiments of Formula h, r=2.
In some embodiments of Formula h, r=3.
In some embodiments of Formula h, r=4.
In some embodiments of Formula h, r>0 and at least one R² is D.

In some embodiments of Formula h, r>0 and at least one R² is an alkyl or deuterated alkyl having 1-12 carbon atoms.

In some embodiments of Formula h, r>0 and at least one R² is silyl or deuterated silyl.

In some embodiments of Formula h, r>0 and at least one R² is germyl or deuterated germyl.

In some embodiments of Formula h, r>0 and at least one R² is heteroaryl. In some embodiments the heteroaryl is derived from a compound selected from the group consisting carbazole, substituted derivatives thereof, and deuterated analogs thereof.

In some embodiments of Formula I, Ar² has Formula i

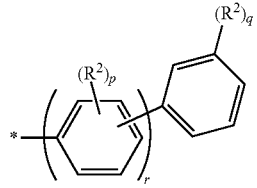

Formula i where R², p, q, r and * are as in Formula h.

The embodiments of R², p, q, and r described above for Formula h apply equally to Formula i.

The embodiments of Ar² described above apply equally to Ar³.

In some embodiments of Formula I, Ar²=Ar³.
In some embodiments of Formula I, Ar²≠Ar³.

In some embodiments, the electroactive compound has Formula II

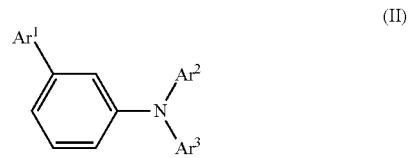

(II)

wherein:
Ar¹ is selected from the group consisting of phenanthrene, triphenylene, triphenylsilyl, triphenylgermyl, dibenzofuran, dibenzothiophene, polyarylphenyl, substituted derivatives thereof, and deuterated analogs thereof;

$Ar^2$ and $Ar^3$ are the same or different and are selected from the group consisting of hydrocarbon aryl, heteroaryl, substituted derivatives thereof, and deuterated analogs thereof, with the proviso that $Ar^2$ and $Ar^3$ are not the same as $Ar^1$; and with the proviso that $Ar^1$, $Ar^2$, and $Ar^3$ have no additional amino substituents.

The embodiments of $Ar^1$, $Ar^2$, and $Ar^3$ described above for Formula I apply equally to Formula II.

Any of the above embodiments for Formula I or Formula II can be combined with one or more of the other embodiments, so long as they are not mutually exclusive. For example, the embodiment in $Ar^1$ is phenanthrene having Formula a can be combined with the embodiment in which b1>0 and at least one $R^1$ is an alkyl or deuterated alkyl having 1-12 carbons and the embodiment in which b2=0. The same is true for the other non-mutually-exclusive embodiments discussed above. The skilled person would understand which embodiments were mutually exclusive and would thus readily be able to determine the combinations of embodiments that are contemplated by the present application.

The compounds of Formula I or Formula II can be made using any technique that will yield a C—C or C—N bond. A variety of such techniques are known, such as Suzuki, Yamamoto, Stille, and metal-catalyzed C—N couplings as well as metal catalyzed and oxidative direct arylation.

Deuterated compounds can be prepared in a similar manner using deuterated precursor materials or, more generally, by treating the non-deuterated compound with deuterated solvent, such as benzene-d6, in the presence of a Lewis acid H/D exchange catalyst, such as trifluoromethanesulfonic acid, aluminum trichloride or ethyl aluminum dichloride.

Exemplary preparations are given in the Examples.

Some non-limiting examples of compounds having Formula I are shown below.

Compound 1

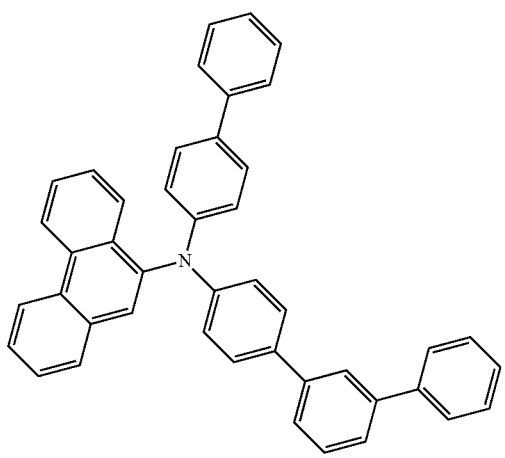

Compound 2

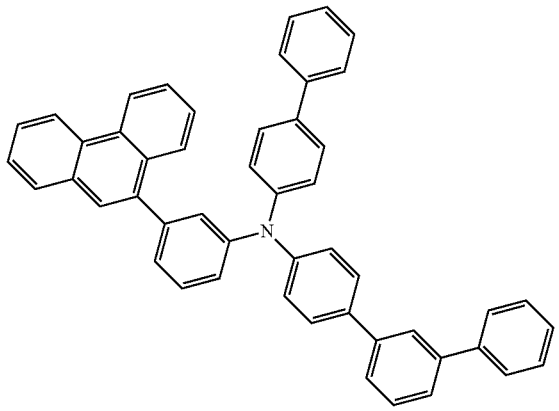

Compound 3

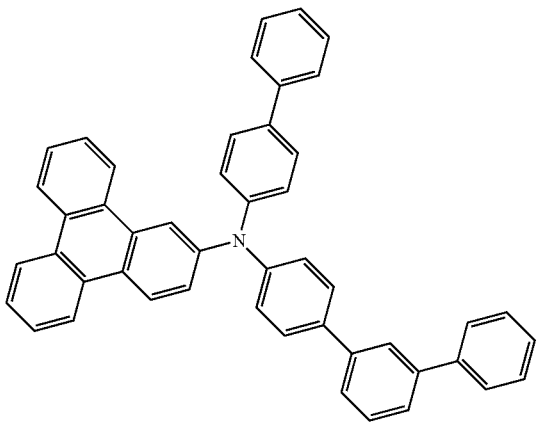

Compound 4

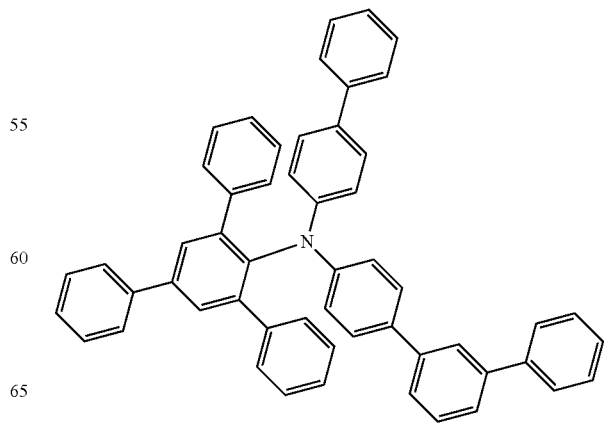

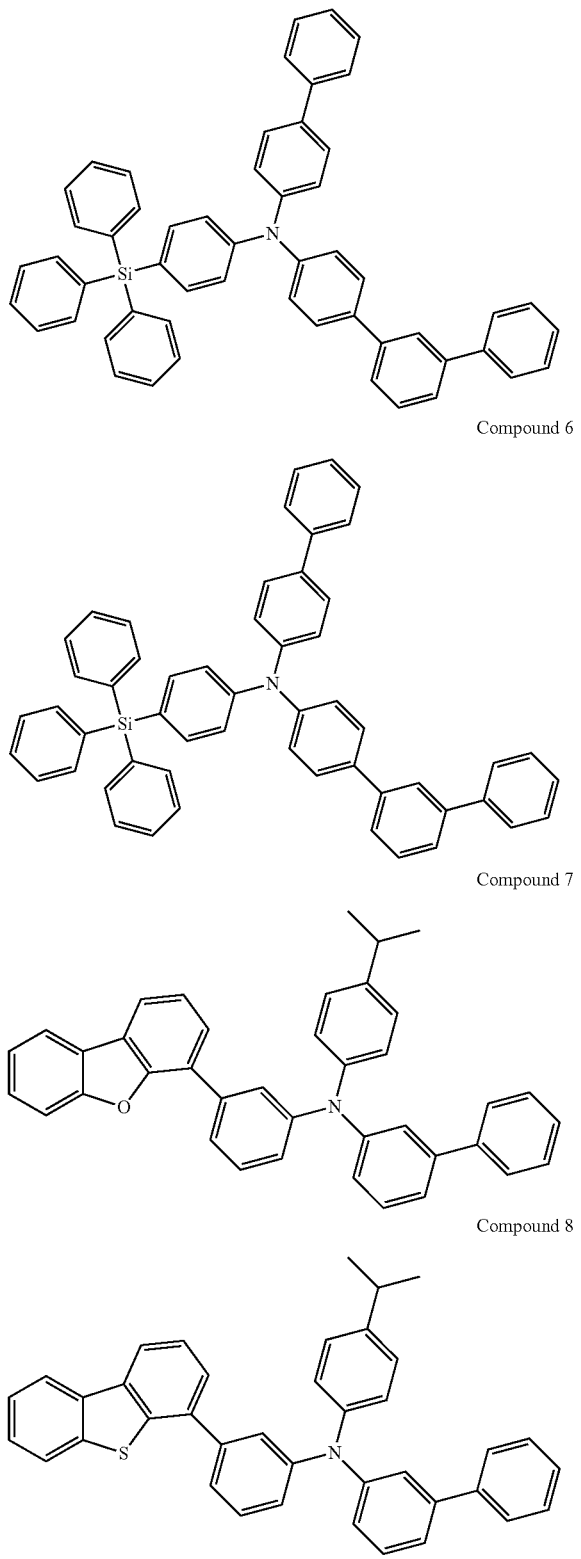

Compound 5

Compound 6

Compound 7

Compound 8

The compounds can be formed into layers for electronic devices. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous liquid deposition techniques, include but are not limited to, spin coating, gravure coating, curtain coating, dip coating, slot-die coating, spray coating, and continuous nozzle coating. Discontinuous liquid deposition techniques include, but are not limited to, ink jet printing, gravure printing, and screen printing.

In some embodiments, the new compounds having Formula I have high triplet energy levels. In some embodiments, the first triplet energy level is at least 2.4 eV.

In some embodiments, the new compounds having Formula I have sufficient solubility in common organic solvents to allow for solution processing. In some embodiments, the solubility in toluene is at least 20 mg/ml.

In some embodiments, the new compounds having Formula I have a Tg sufficient to allow for heated drying of subsequent layers in devices. In some embodiments, the Tg is at least 90° C.

In some embodiments, the new compounds having Formula I can be used as hole transport materials in devices.

In some embodiments, the new compounds having Formula I are electroluminescent and can be used as emissive materials in devices.

In some embodiments, the new compounds having Formula I can be used as hosts for electroluminescent materials.

In some embodiments, the new compounds having Formula I can be used as electron transport materials in devices.

3. Electronic Devices

Organic electronic devices that may benefit from having one or more layers including at least one compound as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), (4) devices that convert light of one wavelength to light of a longer wavelength, (e.g., a down-converting phosphor device); and (5) devices that include one or more electronic components that include one or more organic semi-conductor layers (e.g., a transistor or diode); or any combination of devices in items (1) through (5). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure including at least one compound as described herein, is shown in FIG. 1. The device 100 has a first electrical contact layer, an anode layer 110 and a second electrical contact layer, a cathode layer 160, and a photoactive layer 140 between them. Additional layers may optionally be present. Adjacent to the anode may be a hole injection layer 120, sometimes referred to as a buffer layer. Adjacent to the hole injection layer may be a hole transport layer 130, including hole transport material. Adjacent to the cathode may be an electron transport layer 150, including an electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the organic active layers.

Figure 2:
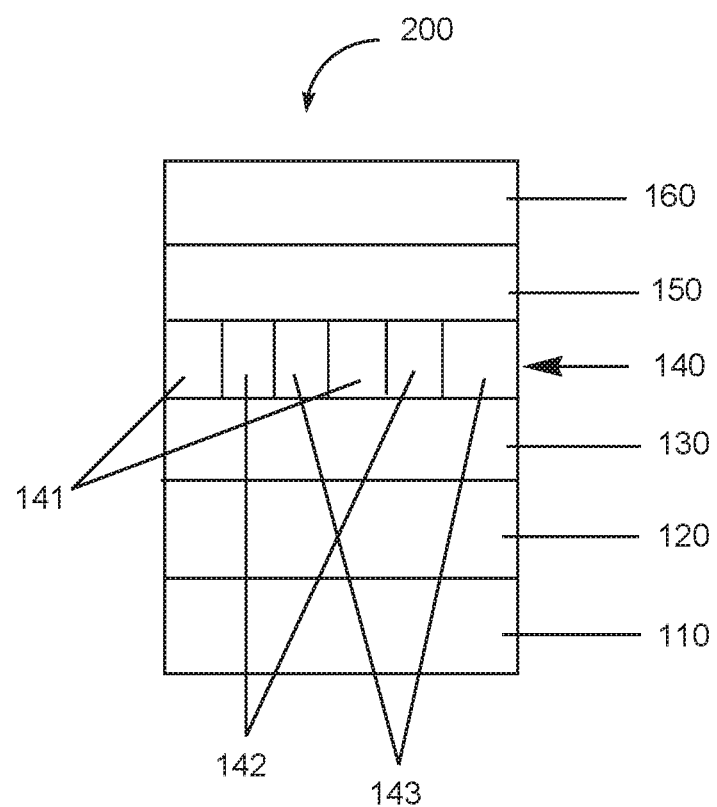
FIG. 2 includes an illustration of another example of an organic electronic device including a new compound described herein.

In some embodiments, in order to achieve full color, the light-emitting layer is pixellated, with subpixel units for each of the different colors. An illustration of a pixellated device is shown in FIG. 2. The device 200 has anode 110, hole injection layer 120, hole transport layer 130, photoactive layer 140, electron transport layer 150, and cathode 160. The photoactive layer is divided into subpixels 141, 142, 143, which are repeated across the layer. In some embodiments, the subpixels represent red, blue and green color emission. Although three different subpixel units are depicted in FIG. 2, two or more than three subpixel units may be used.

Figure 3:
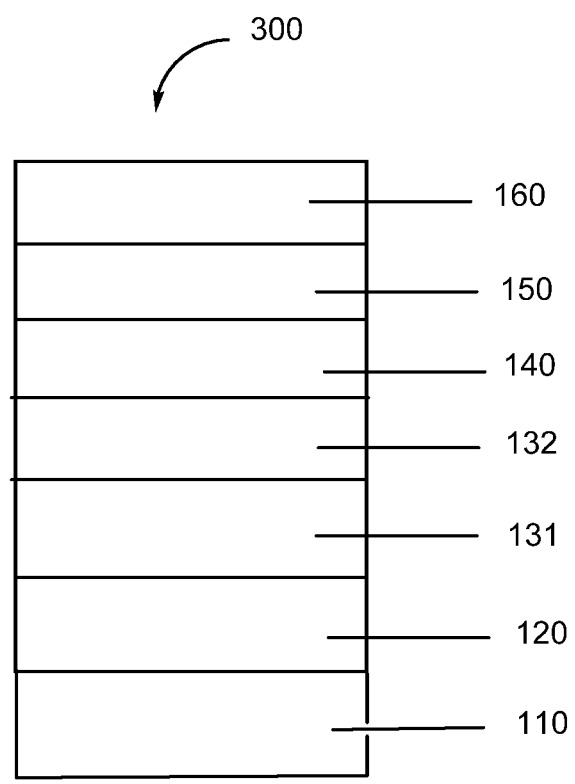
FIG. 3 includes an illustration of another example of an organic electronic device including a new compound described herein.

In some embodiments, the device has the structure shown in FIG. 3. Between hole injection layer 120 and photoactive layer 140 in device 300, there is a first hole transport layer 131 and a second hole transport layer 132. Layers 110, 120, 140, 150, and 160 are as defined in FIG. 1.

Figure 4:
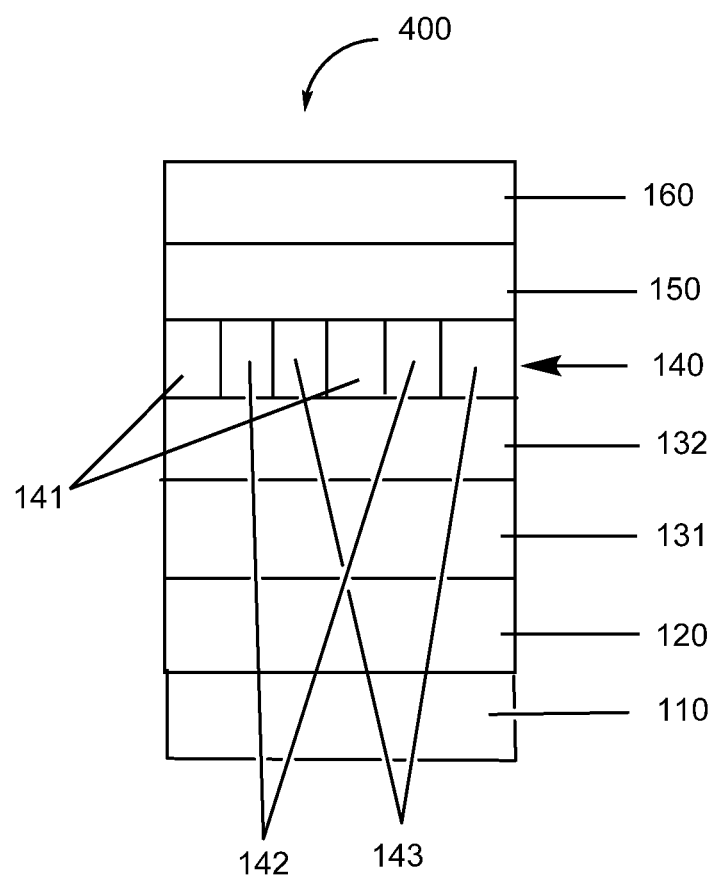
FIG. 4 includes an illustration of another example of an organic electronic device including a new compound described herein.

In some embodiments, the device has the structure shown in FIG. 4. Between hole injection layer 120 and photoactive layer 140 in device 400, there is a first hole transport layer 131 and a second hole transport layer 132. Layers 110, 120, 141, 142, 143, 150, and 160 are as defined in FIG. 2.

The different layers will be discussed further herein with reference to FIG. 1 and FIG. 3. However, the discussion applies to FIG. 2, FIG. 4, and other configurations as well.

In some embodiments, the different layers have the following range of thicknesses: anode 110, 100-5000 Å, in some embodiments, 200-750 Å; hole injection layer 120, 50-2000 Å, in some embodiments, 200-1500 Å; total of hole transport layers 130 or 131+132, 50-3000 Å, in some embodiments, 200-2000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The desired ratio of layer thicknesses will depend on the exact nature of the materials used.

One or more of the new compounds having Formula I described herein may be present in one or more of the electroactive layers of a device.

In some embodiments, devices including the new compounds having Formula I have greater efficiency.

In some embodiments, devices including the new compounds having Formula I have longer lifetime.

In some embodiments, the new compounds having Formula I are useful as hole transport materials in layer 130.

In some embodiments, because the new compounds having Formula I have high triplet energy levels, they are useful as hole transport materials for devices having blue photoactive materials in layer 140.

In some embodiments, the new compounds having Formula I are useful in a second hole transport layer 132 between hole transport layer 131 and photoactive layer 140. The new compounds are particularly useful in a second hole transport layer when the photoactive layer has blue photoactive materials.

In some embodiments, an organic electronic device includes, in order, an anode, a hole transport layer, a photoactive layer, and a cathode, where the hole transport layer includes a compound having Formula I. Additional layers may be present in the device.

In some embodiments, the new compounds having Formula I are useful as host materials for photoactive dopant materials in photoactive layer 140. The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material. The term "host material" is intended to mean a material to which a dopant is added. The host material may or may not have electronic characteristic(s) or the ability to emit, receive, or filter radiation. In some embodiments, the host material is present in higher concentration.

In some embodiments, the new compounds having Formula I are useful as hosts for phosphorescent materials having red, yellow, or green emission color.

In some embodiments, the new compounds having Formula I are useful as a first host material in combination with a second host material. In some embodiments, the second host material is an electron transporting host.

In some embodiments, an organic electronic device includes an anode, a cathode, and at least one organic active layer therebetween, where the organic active layer includes a compound having Formula I.

In some embodiments, an organic electronic device includes an anode, a cathode, and a photoactive layer therebetween, where the photoactive layer includes a compound having Formula I.

In some embodiments, an organic electronic device includes an anode, a cathode, and a photoactive layer therebetween, and further includes an additional organic active layer including a compound having Formula I. In some embodiments, the additional organic active layer is a hole transport layer.

In some embodiments, an organic electronic device includes, in order, an anode, a hole transport layer, a photoactive layer, and a cathode, where the hole transport layer includes a compound having Formula I.

In some embodiments, an organic electronic device includes, in order, an anode, a first hole transport layer, a second hole transport layer, a photoactive layer, and a cathode, where the second hole transport layer includes a compound having Formula I. In some embodiments, the second hole transport layer is directly adjacent to and in contact with the photoactive layer.

In some embodiments, an organic electronic device includes an anode, a hole transport layer, a photoactive layer, and a cathode, where both the hole transport layer and the photoactive layer include a compound having Formula I. In some embodiments, the hole transport layer is directly adjacent to and in contact with the photoactive layer.

In all of the above-described devices, additional layers may be present.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also include an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

Optional hole injection layer 120 includes hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer 120 can include charge transfer compounds, and the like, such as copper phthalocyanine and the tetrathiafulvalene-tetracyanoquinodimethane system (TTF-TCNQ). In some embodiments, the hole injection layer 120 is made from a dispersion of a conducting polymer and a colloid-forming polymeric acid. Such materials have been described in, for example, published U.S. patent applications 2004-0102577, 2004-0127637, and 2005-0205860.

In some embodiments, the hole injection layer is a small molecule. In some embodiments, the hole injection layer is selected from the group consisting of 1,4,5,8,9,11-hexaazatriphenylenehexacarbonitrile, tetracyanoquinodimethane, and tetracyano-2,3,5,6-tetrafluoroquinodimethane.

In some embodiments, an optional short reduction layer (not shown) is present between the anode and the hole injection layer. The short reduction layer includes hole injection material. In some embodiments, the hole injection layer comprises an electrically conductive polymer and a polymeric acid. In some embodiments, the polymeric acid is fluorinated; in some embodiments, at least 90% fluorinated. In some embodiments, the short reduction layer has a greater thickness than the hole injection layer.

Layer 130 includes hole transport material.

In some embodiments, layer 130 includes a compound having Formula I. In some embodiments, layer 130 includes only a compound having Formula I, where additional materials that would materially alter the principle of operation or the distinguishing characteristics of the layer are not present.

In some embodiments, a second hole transport layer 132 is present between hole transport layer 131 and photoactive layer 140, and the second hole transport layer includes a compound having Formula I. In some embodiments, the second hole transport layer 132 includes only a compound having Formula I, where additional materials that would materially alter the principle of operation or the distinguishing characteristics of the layer are not present.

In some embodiments, layer 130 includes other hole transport materials. Examples of hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4',4''-tris(N,N-diphenyl-amino)-triphenylamine (TDATA); 4,4',4''-tris(N-3-methylphenyl-N-phenyl-amino)-triphenylamine (MTDATA); N,N'-diphenyl-N,N'-bis(3-methylphenyl)-[1,1'-biphenyl]-4,4'-diamine (TPD); 4, 4'-bis(carbazol-9-yl)biphenyl (CBP); 1,3-bis(carbazol-9-yl)benzene (mCP); 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); α-phenyl-4-N,N-diphenylaminostyrene (TPS); p-(diethylamino)benzaldehyde diphenylhydrazone (DEH); triphenylamine (TPA); bis[4-(N,N-diethylamino)-2-methylphenyl](4-methylphenyl)methane (MPMP); 1-phenyl-3[p-(diethylamino)styryl]-5-[p-(diethylamino)phenyl] pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Layer 131 can include any of the hole transport materials described above for layer 130.

In some embodiments, layer 131 includes a triarylamine compound, a triarylamine polymer, or deuterated analog thereof.

Depending upon the application of the device, the photoactive layer 140 can be a light-emitting layer that is activated by an applied voltage (such as in a light-emitting diode or light-emitting electrochemical cell), a layer of material that absorbs light and emits light having a longer wavelength (such as in a down-converting phosphor device), or a layer of material that responds to radiant energy and generates a signal with or without an applied bias voltage (such as in a photodetector or photovoltaic device).

In some embodiments, the photoactive layer includes a compound having Formula I as host material and additionally includes a photoactive dopant. The photoactive dopant can be an organic electroluminescent ("EL") material. Any EL material can be used in the devices, including, but not limited to, small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, benzofluorenes, stilbenes, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. In some cases the small molecule fluorescent or organometallic materials are deposited as a dopant with a host material to improve processing and/or electronic properties. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In some embodiments, photoactive layer 140 includes a photoactive dopant and a host material having Formula I. In some embodiments, photoactive layer 140 includes only a photoactive dopant and a host material having Formula I, where additional materials that would materially alter the principle of operation or the distinguishing characteristics of the layer are not present.

In some embodiments, photoactive layer 140 includes a photoactive dopant, a host material having Formula I, and a second host material. Examples of second host materials include, but are not limited to, quinoxalines, phenylpyridines, indolocarbazoles, indoloindoles, and metal quinolinate complexes, substituted derivatives thereof, and deuterated analogs thereof.

In some embodiments, the second host is selected from the group consisting of chrysenes, phenanthrenes, triphenylenes, phenanthrolines, triazines, naphthalenes, anthracenes, quinolines, isoquinolines, quinoxalines, phenylpyridines, carbazoles, indolocarbazoles, indoloindoles, furans, benzofurans, dibenzofurans, benzodifurans, metal quinolinate complexes, substituted derivatives thereof, and deuterated analogs thereof.

In some embodiments, the second host is selected from the group consisting of triphenylenes, carbazoles, indolocarbazoles, indoloindoles, furans, benzofurans, dibenzofurans, substituted derivatives thereof, and deuterated analogs thereof.

In some embodiments, photoactive layer 140 includes only a photoactive dopant, a first host material having Formula I, and a second host material, where additional materials that would materially alter the principle of operation or the distinguishing characteristics of the layer are not present.

Optional layer 150 can function both to facilitate electron transport, and also serve as a confinement layer to prevent quenching of the exciton at layer interfaces. Preferably, this layer promotes electron mobility and reduces exciton quenching.

In some embodiments, layer 150 includes other electron transport materials. Examples of electron transport materials which can be used in the optional electron transport layer 150, include metal chelated oxinoid compounds, including metal quinolate derivatives such as tris(8-hydroxyquinolato) aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato) zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

An optional electron injection layer may be deposited over the electron transport layer. Examples of electron injection materials include, but are not limited to, Li-containing organometallic compounds, LiF, $Li_2O$, Li quinolate, Cs-containing organometallic compounds, CsF, $Cs_2O$, and $Cs_2CO_3$. This layer may react with the underlying electron transport layer, the overlying cathode, or both. When an electron injection layer is present, the amount of material deposited is generally in the range of 1-100 Å, in some embodiments 1-10 Å.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

For liquid deposition methods, a suitable solvent for a particular compound or related class of compounds can be readily determined by one skilled in the art. For some applications, it is desirable that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics such as toluene, xylenes, trifluorotoluene and the like. Other suitable liquids for use in making the liquid composition, either as a solution or dispersion as described herein, including the new compounds, includes, but not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methyl pyrrolidone) esters (such as ethylacetate) alcohols (isopropanol), ketones (cyclopentatone) and mixtures thereof. Suitable solvents for electroluminescent materials have been described in, for example, published PCT application WO 2007/145979.

In some embodiments, the device is fabricated by liquid deposition of the hole injection layer, the hole transport layer, and the photoactive layer, and by vapor deposition of the anode, the electron transport layer, an electron injection layer and the cathode.

It is understood that the efficiency of devices made with the new compositions described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In some embodiments, the device has the following structure, in order: anode, hole injection layer, hole transport layer, photoactive layer, electron transport layer, electron injection layer, cathode.

In some embodiments, the device has the following structure, in order: anode, short reduction layer, hole injection layer, hole transport layer, photoactive layer, electron transport layer, electron injection layer, cathode.

In some embodiments, the device has the following structure, in order: anode, hole injection layer, first hole transport layer, second hole transport layer, photoactive layer, electron transport layer, electron injection layer, cathode.

Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Synthesis Example 1

This example illustrates the preparation of compounds having Formula I, where a=0.

The compounds can generally be prepared according to Scheme 1 or Scheme 2 shown below.

Scheme 1

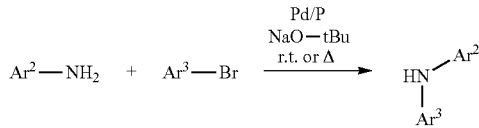

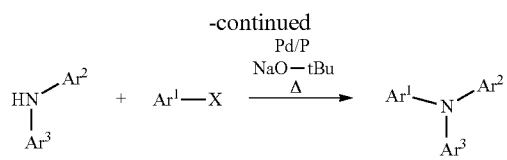

Scheme 2

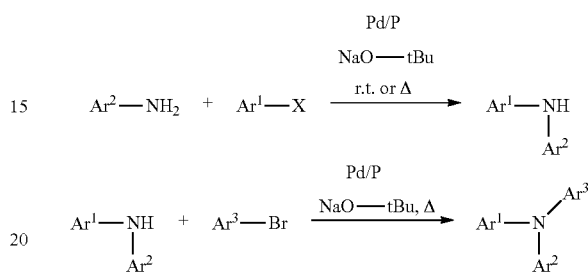

In the above schemes: $Ar^1$, $Ar^2$, and $Ar^3$ are as defined in Formula I; Pd/P represents a palladium catalyst in combination with a phosphine compound; X=halide; r.t. represents room temperature; and Δ represents heating. In some embodiments, the heating temperature is 50-100° C.; in some embodiments, 70-90° C.

Synthesis Example 2

This example illustrates the preparation of compounds having Formula I, where a=1.

The compounds can generally be prepared according to Scheme 3 shown below.

Scheme 3

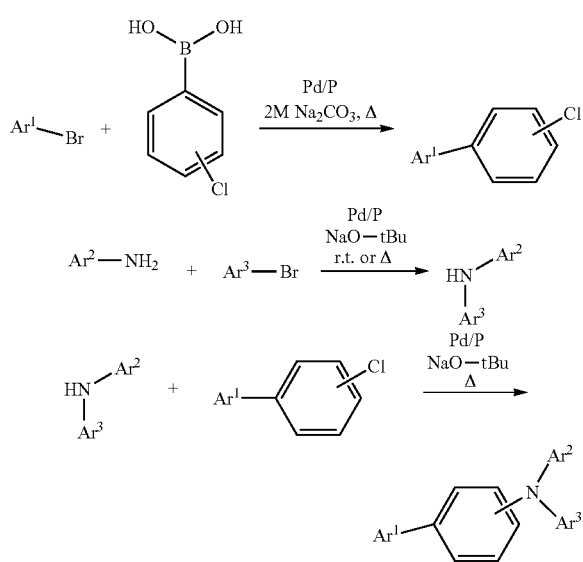

In the above scheme: $Ar^1$, $Ar^2$, and $Ar^3$ are as defined in Formula I; Pd/P represents a palladium catalyst in combination with a phosphine compound; X=halide; r.t. represents room temperature; and Δ represents heating. In some embodiments, the heating temperature is 50-100° C.; in some embodiments, 70-90° C.

Synthesis Example 3

This example illustrates the preparation of a compound having Formula I, Compound 2.

Step 1

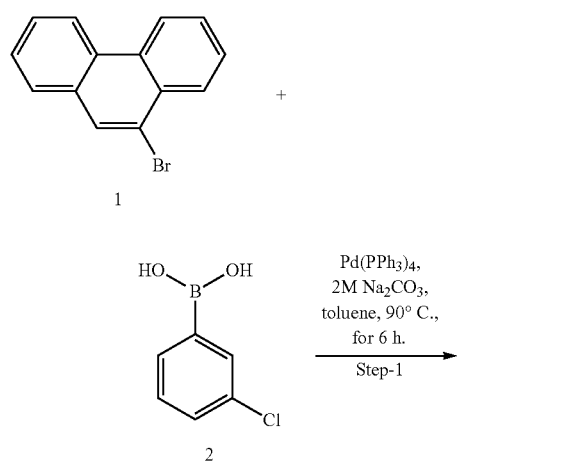

Equimolar amounts of materials 1 and 2 were dissolved in toluene and stirred until the solution was clear. To this was added 4 mol equivalents of 2M Na$_2$CO$_3$ solution and the solution was sparged with argon for 30 min. To this was added 0.05 mol equivalents of Pd(PPh$_3$)$_4$ and the mixture stirred for 6 h at 90° C.

After cooling to room temperature, the reaction mixture was filtered through celite/florisil/silica pad and washed with ethyl acetate. The filtrate was washed with water and brine solution. The organic layer was dried with anhydrous Na$_2$SO$_4$ and concentrated under reduced pressure to obtain the crude material 3. The crude material was purified by one-time column chromatography using 230-400 silica gel and the column was eluted with pet ether to get the pure compound.

Step 2

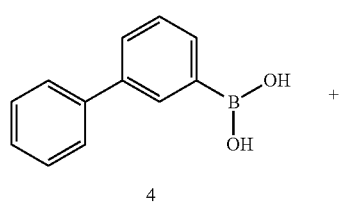

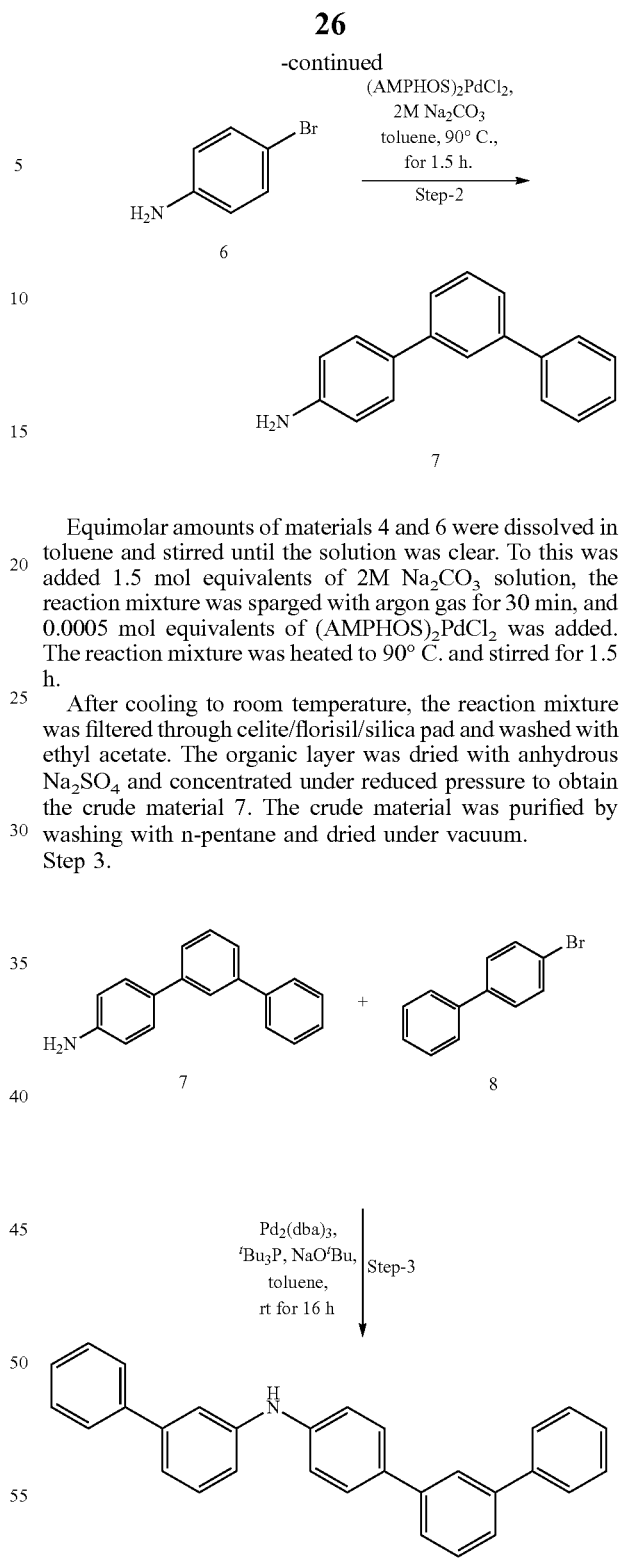

Equimolar amounts of materials 4 and 6 were dissolved in toluene and stirred until the solution was clear. To this was added 1.5 mol equivalents of 2M Na$_2$CO$_3$ solution, the reaction mixture was sparged with argon gas for 30 min, and 0.0005 mol equivalents of (AMPHOS)$_2$PdCl$_2$ was added. The reaction mixture was heated to 90° C. and stirred for 1.5 h.

After cooling to room temperature, the reaction mixture was filtered through celite/florisil/silica pad and washed with ethyl acetate. The organic layer was dried with anhydrous Na$_2$SO$_4$ and concentrated under reduced pressure to obtain the crude material 7. The crude material was purified by washing with n-pentane and dried under vacuum.

Step 3.

Equimolar amounts of materials 7 and 8 were dissolved in anhydrous toluene under nitrogen and stirred until the solution was clear. To this was added 1.5 mol equivalents of NaOt-Bu, 0.05 mol equivalents of Pd$_2$(dba)$_3$ and 0.1 mol equivalents of t-Bu$_3$P (50% w/w in toluene), and the resulting reaction mixture was stirred for 16 h at room temperature.

The reaction mixture was diluted with ethyl acetate, brine solution and filtered through celite/florisil/silica pad and washed with ethyl acetate. The organic layer was separated, dried over anhydrous Na₂SO₄ and concentrated under reduced pressure to get the crude material 10. The crude material was purified by washings with acetonitrile, dried, and again washed with toluene to get pure material.

Step 4.

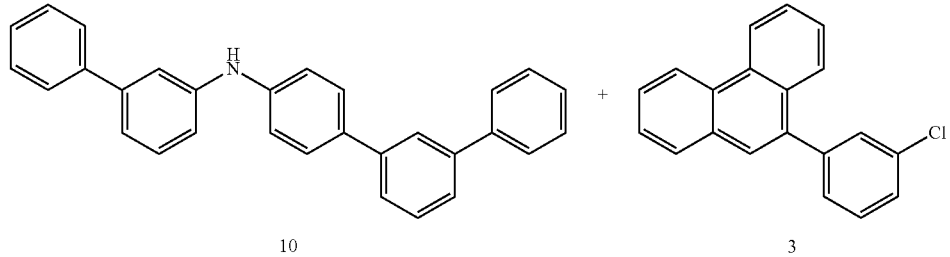

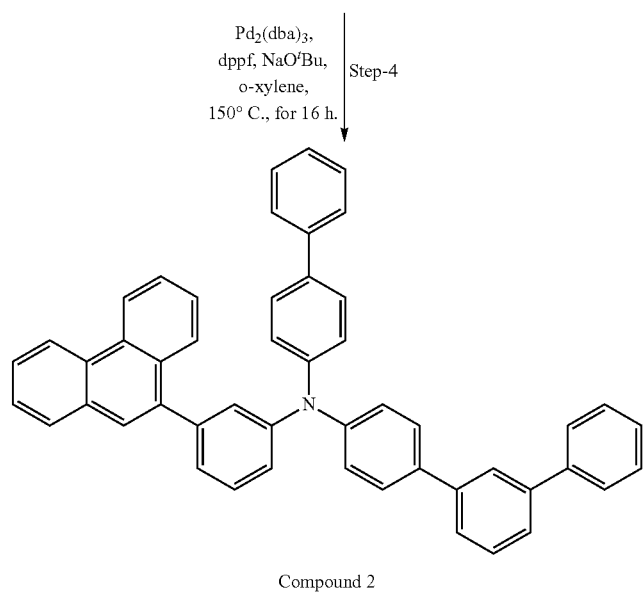

Compound 2

1 mol equivalent of material 10 and 1.2 mol equivalents of material 3 were dissolved in anhydrouse o-xylene under nitrogen and stirred until the solution was clear. To this was added 2 mol equivalents of NaOt-Bu, 0.05 mol equivalents of Pd₂(dba)₃ and 0.1 mol equivalents of 1,1-bis(diphenylphosphino)ferrocene, and the resulting reaction mixture was stirred for 16 h at 150° C.

The reaction mixture was allowed to cool to room temperature, diluted with ethyl acetate and diluted with brine solution (degassed with argon). The reaction mixture was then filtered through celite/florisil/silica pad and washed with ethyl acetate. The organic layer was separated, dried over anhydrous Na₂SO₄ and concentrated under reduced pressure to minimize the o-xylene volume.

The reaction mixture in o-xylene was poured in to pet ether and stirred for 1 h. The resulting solid was filtered, washed with acetonitrile and dried. The compound was then purified by column chromatography (silica 230-400 mesh) and the column was gradually eluted with 30% CH₂Cl₂ in pet ether. The column fractions were evaporated under reduced pressure. The resulting solid was washed with n-pentane and dried to get >99% purity by UPLC.

Compound 2 was further purified by adding ethanol (30 volumes) and heating to reflux for 20 minutes. At the same temperature toluene (18 volumes) was slowly added, and then again the temperature was brought to 120° C. (internal temperature) for 15 min. After that, the reaction mixture was brought to 35° C. and kept at that temperature for 3 h. The mixture was filtered to collect the solid. The solid was again washed with ethanol (4 vol) to get the pure Compound 2. The pure compound was dried under vacuum (0.05 mm of Hg) for 4 h.

Synthesis Example 4

This example illustrates the preparation of a compound having Formula I, Compound 1.

Step 1.

The secondary amine, material 10, was made as in Synthesis Example 3.

Step 2.

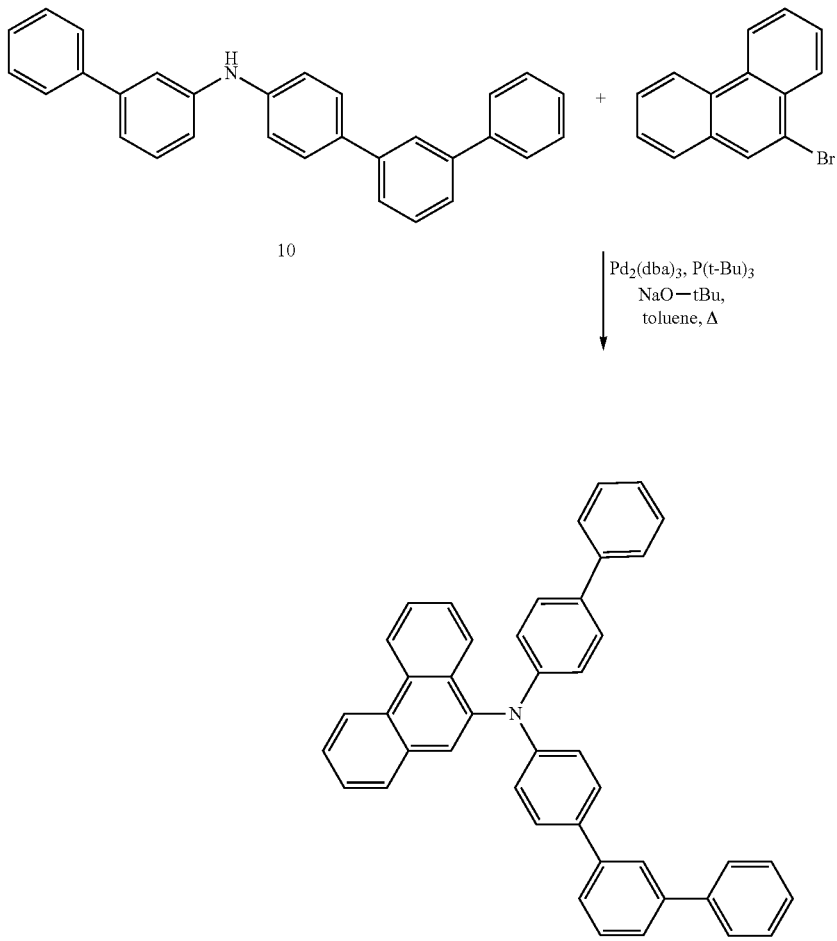

Equimolar amounts of secondary amine 10 and 9-bromophenanthrene were dissolved in anhydrous toluene under nitrogen and stirred until the solution was clear. To this was added 1.2 mol equivalents of NaO⁻tBu, 0.05 mol equivalents of $Pd_2(dba)_3$ and 0.1 mol equivalents of $P(t-Bu)_3$. The resulting reaction mixture was stirred overnight at 90° C.

The resulting mixture was allowed to cool to room temperature, filtered through celite/florisil/silica pad, washed and concentrated. The product was purified by column chromatography.

Synthesis Example 5

This example illustrates the preparation of a compound having Formula I, Compound 4.

The compound can be prepared according to the following scheme.

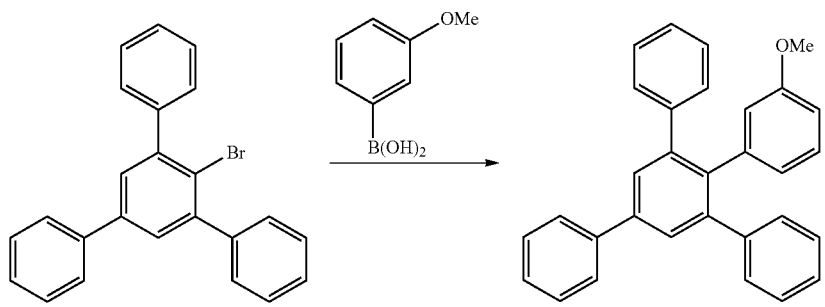

-continued
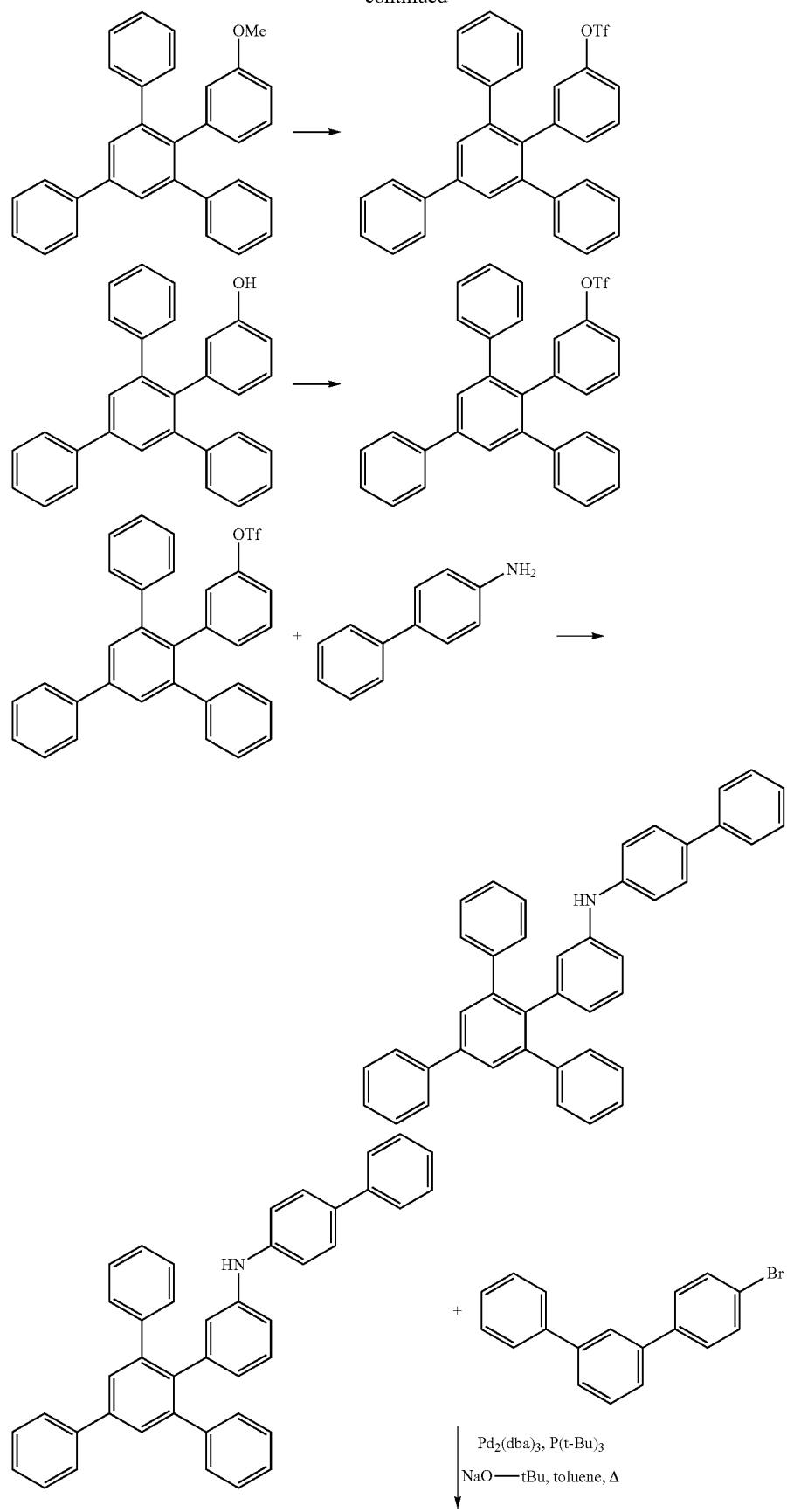

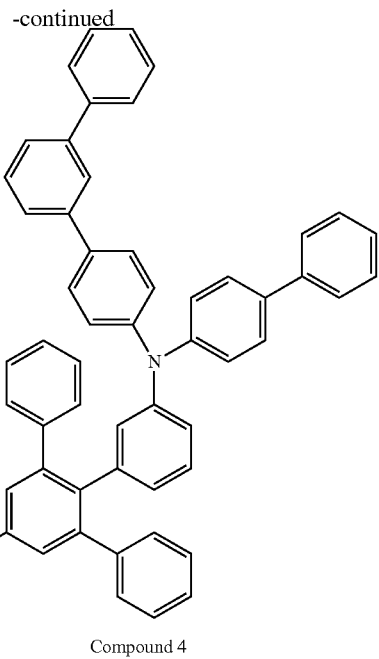

Compound 4

Device Examples (1) Materials

Dopant D1 is a bis(diarylamino)benzofluorene. Such materials have been described in, for example, U.S. Pat. No. 8,465,848.

Dopant D2 is a cyclometallated iridium complex having yellow emission.

ET-1 is an azine-substituted fluoranthene

ET-2 is lithium quinolate.

ET-3 is an aryl phosphine oxide.

HIJ-1 is a hole injection material which is made from an aqueous dispersion of an electrically conductive polymer and a polymeric fluorinated sulfonic acid.

HIJ-2 is 1,4,5,8,9,12-hexaazatriphenylenehexacarbonitrile.

Host H1 is a deuterated diaryl anthracene. The compound can be made using known C—C coupling techniques.

Host H2 is a deuterated indolocarbazole having an N-heteroaryl substituent. The host can be made using known C—C and C—N coupling techniques.

HTM-1 is a triarylamine polymer. The polymer can be made using known C—C and C—N coupling techniques.

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Device Type 1: Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent, to form a hole injection layer ("HIL"). After cooling, the workpieces were then spin-coated with a solution of first hole transport material in anisole:toluene (9:1 v/v) and then heated to remove solvent, to form a first hole transport layer ("HTL1"). In the examples of the invention, the cooled workpieces were then spin-coated with a solution of second hole transport material and heated to remove solvent, to form a second hole transport layer ("HTL2"). In the comparative examples, HTL1 was the only hole transport layer. After cooling, the workpieces were then spin-coated with a solution of the photoactive and host materials in methylbenzoate, to form the photoactive layer or emissive layer ("EML"). The workpieces were then placed in a vacuum chamber and the electron transport materials, electron injection materials, and the Al cathode were then deposited sequentially by thermal evaporation using the appropriate masks, to form the electron transport layer ("ETU"), and the electron injection layer ("EIL"), followed by the cathode. The chamber was vented, and the devices were encapsulated using a glass lid, desiccant, and UV curable epoxy.

Device Type 2: Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent, to form a short reduction layer ("SRL"). The workpieces were then placed in a vacuum chamber. The hole injection material, one or more hole transport materials, the photoactive and host materials, electron transport materials, electron injection material, and the Al cathode were then deposited sequentially by thermal evaporation using the appropriate masks, to form the hole injection layer ("HIL"), one or more hole transport layers ("HTL"), the photoactive layer or emissive layer ("EML"), the electron transport layer ("ETL"), and the electron injection layer ("EIL"), followed by the cathode. The chamber was vented, and the devices were encapsulated using a glass lid, desiccant, and UV curable epoxy.

(3) Device Characterization

The OLED devices were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The color coordinates were determined using either a Minolta CS-100 meter or a Photoresearch PR-705 meter.

Device Example 1 and Comparative Example A

This example illustrates the performance of a device having a second hole transport layer including the new compound having Formula I.

The device was made as described in Device Type 1, with the device structure, in order (all percentages are by weight, based on the total weight of the layer):

Glass Substrate
Anode: ITO (50 nm)
HIL: HIJ-1 (100 nm)
HTL1

Example 1: HTM-1 (85 nm)

Comparative A: HTM-1 (105 nm)
HTL2

Example 1: Compound 2 (20 nm)

Comparative A: none
EML: H1:D1 in 13:1 weight ratio (33 nm)
ETL: ET-1 (20 nm)
EIL: ET-2 (3.8 nm)
Cathode: Al (100 nm)
The results are given in Table 1.

TABLE 1

| Ex. | CE cd/A | EQE (%) | CIEx | CIEy | V | Lum. | T80 |
|---|---|---|---|---|---|---|---|
| A | 8.3 | 9.2 | 0.140 | 0.101 | 4.3 | 1369 | 740 |
| 1 | 9.9 | 11.8 | 0.142 | 0.092 | 4.4 | 1634 | 1500 |

All data at 1000 nits, unless otherwise specified. CE is the current efficiency; EQE = external quantum efficiency; CIEx and CIEy refer to the x and y color coordinates according to the C.I.E. chromaticity scale (Commission Internationale de L'Eclairage, 1931); V is the voltage @ 15 mA/cm$^2$; Lum. is the lifetest luminance in nits; T80 is the time in hours for a device to reach 80% of the initial luminance at a current density of 16.5 mA/cm$^2$ and 50° C.

Device Example 2 and Comparative Example B

This example illustrates the performance of a device having a second hole transport layer including the new compound having Formula I.

The device was made as described in Device Type 1, with the device structure, in order (all percentages are by weight, based on the total weight of the layer):

Glass Substrate
Anode: ITO (50 nm)
HIL: HIJ-1 (100 nm)
HTL1

Example 1: HTM-1 (85 nm)

Comparative B: HTM-1 (105 nm)
HTL2

Example 1: Compound 1 (20 nm)

Comparative B: none
EML: H1:D1 in 13:1 weight ratio (33 nm)
ETL: ET-1 (20 nm)
EIL: ET-2 (3.8 nm)
Cathode: Al (100 nm)
The results are given in Table 2.

TABLE 2

| Ex. | C.E. | EQE (%) | CIEx | CIEy | V | Lum. | T80 |
|---|---|---|---|---|---|---|---|
| B | 8.0 | 8.9 | 0.139 | 0.101 | 4.5 | 1316 | 860 |
| 2 | 9.4 | 10.7 | 0.139 | 0.100 | 4.6 | 1565 | 1360 |

All data at 1000 nits, unless otherwise specified. CE is the current efficiency; EQE = external quantum efficiency; CIEx and CIEy refer to the x and y color coordinates according to the C.I.E. chromaticity scale (Commission Internationale de L'Eclairage, 1931); V is the voltage @ 15 mA/cm$^2$; Lum. is the lifetest luminance in nits; T80 is the time in hours for a device to reach 80% of the initial luminance at a current density of 16.5 mA/cm$^2$ and 50° C.

It can be seen from the results in Tables 1 and 2, that device efficiency and lifetime are increased when the device has a second hole transport layer including a compound having Formula I.

Device Examples 3 and 4 and Comparative Example C

This example illustrates the performance of a device including the new compound having Formula I in the hole transport layer and as a cohost in the photoactive layer.

The device was made as described in Device Type 2, with the device structure, in order (all percentages are by weight, based on the total weight of the layer):

Glass Substrate
Anode: ITO (50 nm)
SRL: HIJ-1 (60 nm)
HIL: HIJ-2 (5 nm)
HTL: Compound 2 (30 nm)
EML: 16% D2 in the host shown in Table 3 below (30 nm)
ETL: ET-3:ET-2 in 3:2 weight ratio
EIL: ET-2 (ETL+EIL=40 nm)
Cathode: Al (100 nm)
The results are shown in Table 3.

TABLE 3

| Ex. | Host | C.E. | EQE (%) | V | T95 |
|---|---|---|---|---|---|
| C | 84% H2 | 93.5 | 27.8 | 4.35 | 870 |
| 3 | 10% Compound 2 74% H2 | 94 | 27.5 | 3.9 | 1780 |

TABLE 3-continued

Device results

| Ex. | Host | C.E. | EQE (%) | V | T95 |
|---|---|---|---|---|---|
| 4 | 30% Compound 2 54% H2 | 83 | 24.5 | 4.1 | 2150 |

All data at 3000 nits, unless otherwise specified. CE is the current efficiency; EQE = external quantum efficiency; V is the; T95 is the time in hours for a device to reach 95% of the initial luminance at a current density of 10 mA/cm².

It can be seen from the results in Table 3, that device lifetime is increased when the device has a host material having Formula I, where the hole transport layer also includes a compound having Formula I.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A organic electronic device comprising:
  only one photoactive layer; and
  a hole transport layer,
  wherein the photoactive layer comprises a photoactive dopant, a host material that is a compound of Formula I

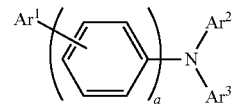

(I)

wherein:
  $Ar^1$ is selected from the group consisting of dibenzofuran having Formula e, dibenzothiophene having Formula f, and deuterated analogs thereof;

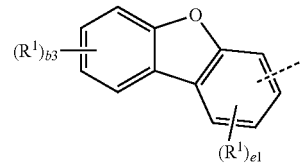

Formula e

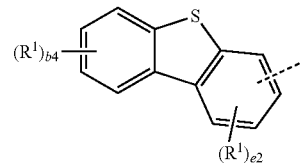

Formula f where:
  $R^1$ is the same or different at each occurrence and is selected from the group consisting of D, alkyl, hydrocarbon aryl, heteroaryl, deuterated alkyl, deuterated hydrocarbon aryl, and deuterated heteroaryl;
  b3 and b4 are 0;
  e1 and e2 are the same or different and are an integer from 1-3; and
  the dashed line represents a possible point of attachment;
  $Ar^2$ is represented by Formula h

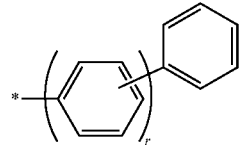

Formula h where:
  r is 1; and
  *indicates the point of attachment,
  $Ar^3$ is represented by Formula h'

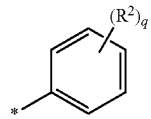

Formula h' where:
  q is 1;
  $R^2$ is alkyl, or deuterated alkyl;
  *indicates the point of attachment; and
  a is 0 or 1.

2. The device of claim 1, wherein $Ar^1$ is a dibenzofuran having Formula e.

3. The device of claim 1, wherein $Ar^1$ a dibenzothiophene having Formula f.

4. The device of claim 1, further comprising:
an anode; and
a cathode,
wherein the hole transport layer comprises one of the following Compound 7 or Compound 8:

Compound 7

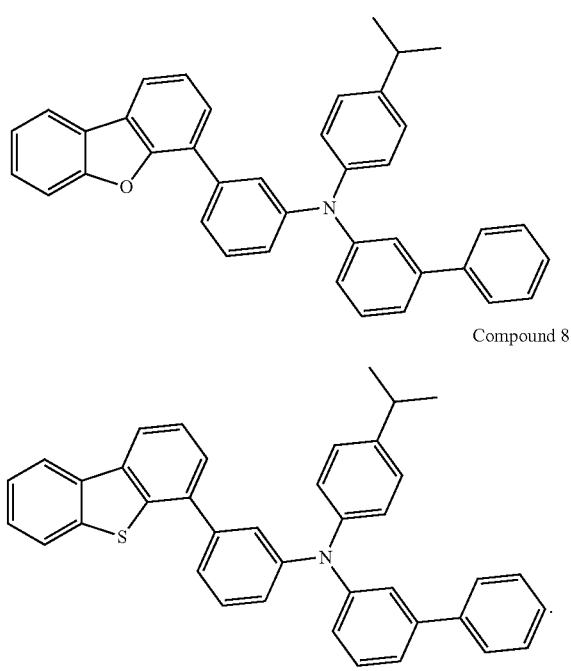

Compound 8

5. The device of claim 1, consisting of an anode, the hole transport layer, the photoactive layer and a cathode.

6. The device of claim 4, wherein the hole transport layer is directly adjacent to and in contact with the photoactive layer.

7. The device of claim 1, further comprising:
an anode; and
a cathode,
wherein the hole transport layer consists of a first hole transport layer and a second hole transport layer,
wherein the second hole transport layer comprises one of the following Compound 7 or Compound 8:

Compound 7

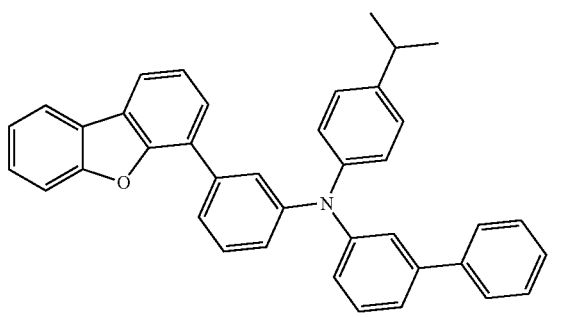

Compound 8

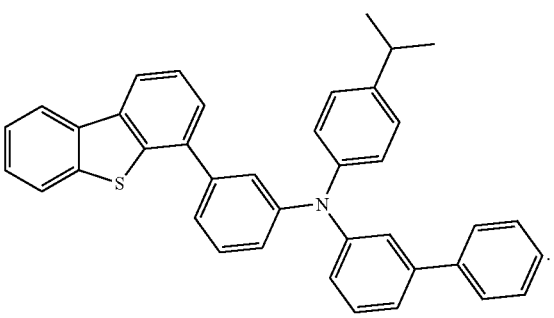

8. The device of claim 7, wherein the second hole transport layer is directly adjacent to and in contact with the photoactive layer.

9. The device of claim 1, further comprising:
an anode; and
a cathode.

10. The device of claim 1, wherein the photoactive layer of claim 1 comprises a second host material,
wherein the second host material is selected from the group consisting of triphenylene, furan, benzofuran, substituted derivatives thereof, and deuterated analogs thereof.

11. The device of claim 1, wherein the hole transport layer comprises a hole transport material comprising a triarylamine polymer, a triarylamine-fluorine copolymer, or deuterated analogs thereof.

* * * * *